United States Patent
McGovern

(10) Patent No.: US 6,380,217 B1
(45) Date of Patent: Apr. 30, 2002

(54) METHODS FOR CONTROLLING GGT-POSITIVE BACTERIA

(75) Inventor: Karen J. McGovern, Littleton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/536,270

(22) Filed: Mar. 27, 2000

Related U.S. Application Data
(60) Provisional application No. 60/127,036, filed on Mar. 31, 1999.

(51) Int. Cl.$^7$ ..................... A61K 31/445; A61K 31/44; A61K 31/425
(52) U.S. Cl. ................. 514/325; 514/290; 514/365
(58) Field of Search ................ 514/325, 365, 514/290

(56) References Cited

U.S. PATENT DOCUMENTS
4,565,818 A * 1/1986 Nordman et al. ........... 514/290

FOREIGN PATENT DOCUMENTS
JP 11071361 * 3/1999

OTHER PUBLICATIONS

Berge, Stephen M., et al., "Pharmaceutical Salts", *Journal of Pharmaceutical Sciences*, 66:1–19 (1977).

Blaser, M.J., "*Helicobactor pylori*: microbiology of a 'slow' bacterial infection", *Trends in Microbiology*, 1:255–260 (1993).

Borén, T., et al., "Attachment of *Helicobacter pylori* to Human Gastric Epithelium Mediated by Blood Group Antigens", *Science*, 262:1892–1895 (1993).

Dick–Hegedus, E. and Lee, A., "Use of a Mouse Model to Examine Anti–*Helicobacter pylori* Agents", *Scand. J. Gastroenterol.*, 26:909–915 (1991).

Eaton, K.A., et al., "Essential Role of Urease in Pathogenesis of Gastritis Induced by *Helicobacter pylori* in Gnotobiotic Piglets", *Infection and Immunity*, 59:2470–2475 (1991).

Evans, D.G., et al., "Cloning, Nucleotide Sequence, and Expression of a Gene Encoding an Adhesin Subunit Protein of *Helicobacter pylori*", *Journal of Bacteriology*, 175:674–683 (1993).

Falk, P., et al., "An in vitro adherence assay reveals that *Helicobacter pylori* exhibits cell lineage–specific tropism in the human gastric epithelium", *Proc. Natl. Acad. Sci. USA*, 90:2035–39 (1993).

Ferrero, R.L. and Lee, A., "The Importance of Urease in Acid Protection for the Gastric–colonising Bacteria *Helicobacter pylori* and *Helicobacter felis* sp. nov.", *Microbial Ecology in Health and Disease*, 4:121–134 (1991).

Haas,, R., et al., "Aflagellated mutants of *Helicobacter pylori* generated by genetic transformation of naturally competent strains using transposon shuttle mutagenesis", *Molecular Microbiology*, 8(4):753–760; Vac A (1993).

Hazell, S. L., et al., "*Campylobacter pyloridis* and Gastritis: Association with Intracellular Spaces and Adaptation to an Environment of Mucus as Important Factors in Colonization of the Gastric Epithelium", *The Journal of Infectious Diseseas*, 153:658–663 (1986).

Hopkins R.J. and Morris, J.G, "*Helicobacter pylori*: The Missing Link in Perspective", *The American Journal of Medicine*, 97:265–277 (1994).

Huesca, M., et al., "Therapeutics Used to Alleviate Peptic Ulcers Inhibit *H. pylori* Receptor Binding in vitro", *Zbl. Bakt.*, 280:244–252 (1993).

Labigne, A., et al., "Shuttle Cloning and Nucleotide Sequences of *Helicobacter pylori* Genes Responsible for Urease Activity", *Journal of Bacteriology*, 173:1920–1931 (1991).

Leying, H., et al., "Cloning and genetic characterization of a *Helicobacter pylori* flagellin gene", *Molecular Micrbiology*, 6(19):2863–2874 (1992).

Malfertheiner, P. and Dominguez–Munoz, J.E., "Rationale for Eradication of *Helicobacter pylori* Infection in Duodenal Ulcer Disease", *Clinical Therapeutics*, 15 Supp. B:37–48 (1993).

Marshall, B.J., et al., "Original isolation of *Campylobacter pyloridis* from human gastric mucosa", *Microbios Letters*, 25:83–88 (1984).

Rathbone, et al., "*Campylobacter pyloridis*–A. new factor in peptic ulcer disease?", *Gut*, 27:635–641 (1986).

Schmitt, W. and Haas, R., "Genetic analysis of the *Helicobacter pylori* vacuolating cytotoxin: structural similarities with the IgA protease type of exported protein", *Molecular Microbiology*, 12(2):307–319 (1994).

Taylor, D.N. and Blaser, M.J., "The Epidemiology of *Helicobacter pylori* infection", *Epidemiologic Review*, 13:42–50 (1991).

Warren, J.R. and Marshall, B., "Unidentified Curved Bacilli on Gastric Epithelium in Active Chronic Gastritis", *The Lancet*, 1:1273–1276 (1983).

* cited by examiner

Primary Examiner—Kevin E. Weddington
(74) Attorney, Agent, or Firm—Lahive & Cockfield, LLP; Elizabeth A. Hanley

(57) ABSTRACT

Methods and compositions useful for controlling GGT positive bacteria have been identified.

29 Claims, No Drawings

METHODS FOR CONTROLLING GGT-POSITIVE BACTERIA

RELATED APPLICATION

This application claims priority to U.S. Provisional Application Serial No. 60/127,036, entitled "Methods for Controlling GGT-Positive Bacteria," filed on Mar. 31, 1999; the entire contents of which are hereby incorporated herein by reference.

BACKGROUND

*Helicobacter pylori* bacterial infections are a serious problem in humans. They have been shown to be a strong causative factor in gastric ulcer disease, such as stomach ulcers and small intestine ulcers which can result in death. *Helicobacter pylori* is a gram-negative, S-shaped, microaerophilic bacterium that was discovered and cultured from a human gastric biopsy specimen. (Warren, J. R. and B. Marshall, (1983) *Lancet* 1: 1273–1275; and Marshall et al., (1984) *Microbios Lett.* 25: 83–88). *H. pylori* bacterial cells can survive in a low pH environment because of an enzyme on their outer cell wall called urease. Urease converts urea in the stomach into bicarbonate and ammonia. The bicarbonate and ammonia neutralize the acid gastric juices, thereby providing a protective layer around the *H. pylori*.

Since *H. pylori* are gram-negative rod type bacteria, it is difficult to treat *H. pylori* infections without using agents that will also affect other gram-negative bacteria elsewhere in the body. *H. pylori* has been strongly linked to chronic gastritis and duodenal ulcer disease. (Rathbone et. al., (1986) *Gut* 27: 635–641). Moreover, evidence is accumulating for an etiologic role of *H. pylori* in nonulcer dyspepsia, gastric ulcer disease, and gastric adenocarcinoma. (Blaser M. J., (1993) *Trends Microbiol.* 1: 255–260). Transmission of the bacteria occurs via the oral route, and the risk of infection increases with age. (Taylor, D. N. and M. J. Blaser, (1991) *Epidemiol. Rev* 13: 42–50). *H. pylori* colonizes the human gastric mucosa, establishing an infection that usually persists for decades. Infection by *H. pylori* is prevalent worldwide. Developed countries have infection rates over 50% of the adult population, while developing countries have infection rates reaching 90% of the adults over the age of 20. (Hopkins R. J. and J. G. Morris (1994) *Am. J. Med.* 97: 265–277).

The bacterial factors necessary for colonization of the gastric environment, and for virulence of this pathogen, are poorly understood. Examples of the putative virulence factors include the following: urease, an enzyme that may play a role in neutralizing gastric acid pH (Eaton et al., (1991) *Infect. Immunol.* 59: 2470–2475; Ferrero, R. L. and A. Lee (1991) *Microb. Ecol. Hlth. Dis.* 4: 121–134; Labigne et al., (1991) *J. Bacteriol.* 173: 1920–1931); the bacterial flagellar proteins responsible for motility across the mucous layer (Hazell et al., (1986) *J. Inf. Dis.* 153: 658–663; Leying et al., (1992) *Mol. Microbiol.* 6: 2863–2874; and Haas et al., (1993) *Mol. Microbiol.* 8: 753–760; Vac A), a bacterial toxin that induces the formation of intracellular vacuoles in epithelial cells (Schmitt, W. and R. Haas, (1994) *Molecular Microbiol.* 12(2): 307–319) and several gastric tissue-specific adhesions (Boren et al., (1993) *Science* 262: 1892–1895; Evans et al., (1993) *J. Bacteriol.* 175: 674–683; and Falk et al., (1993) *Proc. Natl. Acad. Sci.* USA 90: 2035–2039).

Certain therapeutic agents are known to eradicate *H. pylori* infections in vitro. (Huesca et. al., (1993) *Zbl. Bakt.* 280: 244–252; Hopkins, R. J. and J. G. Morris, supra). However, many agents are suboptimally effective in vivo because of bacterial resistance, altered drug distribution, patient non-compliance, poor drug availability and lack of selectivity for *H. pylori*. (Hopkins, R. J. and J. G. Morris, supra). Treatment with antibiotics combined with bismuth are part of a standard regime used to treat *H. pylori* infection. (Malfertheiner, P. and J. E. Dominguez-Munoz (1993) *Clinical Therapeutics* 15 Supp. B: 37–48). Recently, combinations of a proton pump inhibitor and a single antibiotic have been shown to ameliorate duodenal ulcer disease. (Malfertheiner, P. and J. E. Dominguez-Munoz supra).

SUMMARY

The invention pertains to a method for controlling GGT-positive bacteria, advantageously *H. pylori*, in a mammal, preferably a human, by administering to the mammal a therapeutically effective amount of a GGT modulating compound.

It also pertains to a method treating a state characterized by the presence of GGT-positive bacteria in a mammal, by administering to a mammal a therapeutically effective amount of a GGT modulating compound.

The invention also includes a method of controlling GGT-positive bacteria by contacting the bacteria with a GGT modulating compound.

In another embodiment, the invention pertains to a pharmaceutical preparation for the treatment of a state characterized by the presence of GGT-positive bacteria in a mammal. The pharmaceutical preparation consists of a therapeutically effective amount of a GGT modulating compound and a pharmaceutically acceptable carrier.

The invention also pertains to a method for controlling *Helicobacter pylori* in a mammal. The method includes administering to the mammal a therapeutically effective amount of a GGT-modulating compound, such that *Helicobacter pylori* in the mammal is controlled.

The invention further pertains to a method for treating an ulcer e.g., an ulcer associated with *H. pylori*, in the gastrointestinal tract of a mammal, by administering to a mammal a therapeutically effective amount of a GGT-modulating compound.

The invention also features a packaged pharmaceutical composition for controlling GGT-positive bacteria in a mammal. The packaged pharmaceutical composition consists of a container holding a therapeutically effective amount of a pharmaceutical composition for treating GGT-positive bacteria in a mammal, the pharmaceutical composition comprising at least one GGT modulating compound, and instructions for using the pharmaceutical composition.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention pertains to a method for controlling GGT-positive bacteria in a mammal, e.g. a human. The method includes administering to a mammal a therapeutically effective amount of a GGT modulating compound.

The term "GGT-positive bacteria" includes bacteria which express gamma glutamyl transpeptidase (GGT). GGT is an enzyme involved in the transfer of glutamic acid from glutathione to other acceptors. It is also involved in the hydrolysis of glutathione and other gamma-glutamyl amino acids and dipeptides, possibly as a means for amino acid uptake. Examples of GGT-positive bacteria include agents associated with disorders of the gastrointestinal tract, e.g., *H. pylori*. For *H. pylori*, GGT has been shown to be an essential colonization factor in mouse models. Therefore, although not wishing to be bound by theory, it has been suggested that GGT inhibiting compounds may control GGT positive bacteria by disrupting the formation of bacterial colonies.

The language "controlling GGT-positive bacteria" includes changes in growth or replication of the GGT positive bacteria or eradication of GGT positive bacteria. The language includes preventing survival or inhibiting continued growth and replication of GGT positive bacteria. In a preferred embodiment, the control of the GGT positive bacteria is such that a GGT positive bacterial infection is treated.

The language "GGT modulating compound" includes compounds which interact with GGT and modulate its activity. In one embodiment, the GGT modulating compound may inhibit GGT activity. Compounds which inhibit GGT activity can be identified through the Cell Based GGT Inhibitor (CBGI) Assay. The CBGI Assay is described in detail in the Example section. The compounds of this invention, e.g., the particular species described herein, can be purchased and/or synthesized using art-recognized techniques. Examples of preferred GGT modulating compounds include:

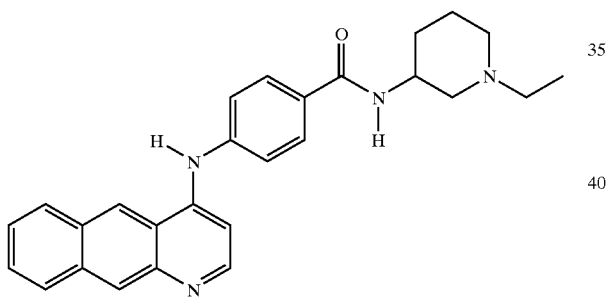

Another preferred GGT-modulating compound is:

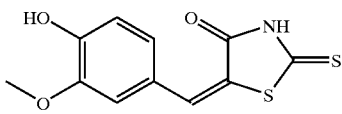

Another preferred GGT modulating compound is:

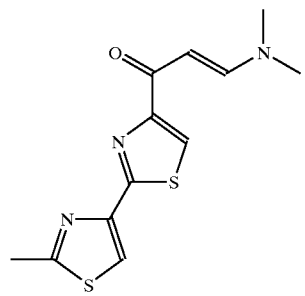

Another preferred GGT modulating compound is:

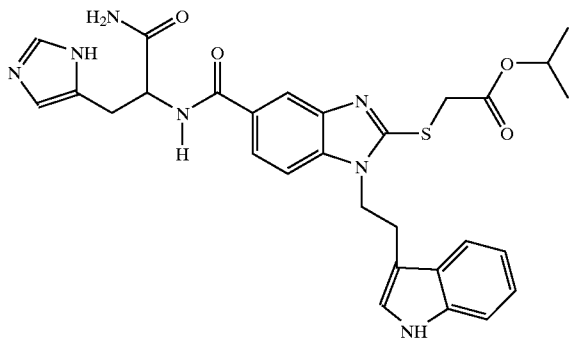

Another preferred GGT modulating compound is:

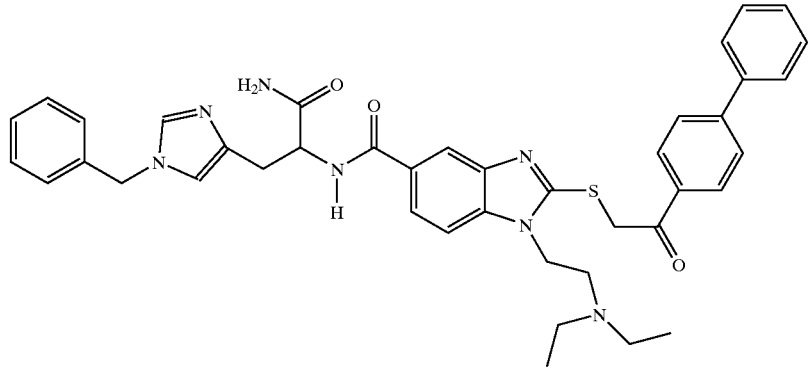

Another preferred GGT modulating compound is:

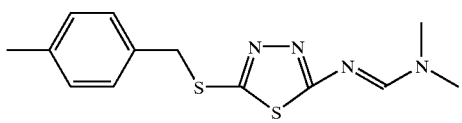

Another preferred GGT modulating compound is:

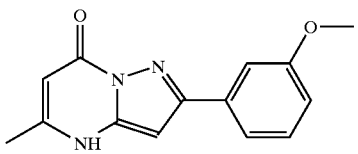

In another embodiment, the invention features a method of treating a state characterized by the presence of GGT-positive bacteria in a mammal. The method includes administering to the mammal a therapeutically effective amount of a GGT modulating compound. Preferably, the GGT-positive bacteria is an agent associated with disorders of the gastrointestinal tract.

The language "state characterized by the presence of GGT positive bacteria" includes those diseases, disorders or conditions which have been associated with a GGT positive bacteria in that the GGT positive bacteria is directly or indirectly a causative agent of the disease, disorder or condition. The GGT positive bacteria does not have to be the sole causative agent of the disease, disorder or condition merely responsible for causing some of the symptoms typically associated with the disease, disorder, or condition being treated. The GGT positive bacteria can be the causative agent alone or at least one other agent can be involved in the state being treated. Examples include ulcers and inflammation and those symptoms not manifested by the presence of ulcerations in the gastric mucosa, such as gastritis, non-ulcer dyspepsia, esophageal reflux disease and peptic ulcer disease. Preferred examples include those symptoms associated with *Helicobacter pylori*.

The language "treating or treatment of the state characterized by the presence of GGT positive bacteria" includes the alleviation of or diminishment of at least one symptom typically associated with the state. The treatment also includes alleviation or diminishment of more than one symptom. Preferably, the treatment cures, e.g., substantially eliminates, the symptoms associated with the state. The treatment also can include the prevention, reduction or elimination of such bacteria and/or the prevention or reduction in colonization of such bacteria.

The term "gastrointestinal tract" includes the digestive system of an animal. The gastrointestinal tract(s) includes the esophagus, stomach and intestine, e.g., small and large.

The phrases "disorders of the gastrointestinal tract" or "gastrointestinal disorders" include physical manifestations caused by a foreign stimulus or by GGT positive bacteria, e.g., *Helicobacter pylori* in the gastrointestinal tract. Gastrointestinal disorders can take the form of inflammation or ulceration of a portion of the gastrointestinal tract or gastritis, non-ulcer dyspepsia, esophageal reflux disease and peptic ulcer disease. Preferred examples include those manifestations caused by or associated with *Helicobacter pylori*.

The language "GGT-positive bacteria which are agents associated with disorders of the gastrointestinal tract" includes those GGT positive bacteria which cause or are associated with disorders of the gastrointestinal tract, including inflammation and/or ulcers. Disorders of the gastrointestinal tract also include those symptoms not manifested by the presence of ulcerations in the gastric mucosa, such as gastritis, non-ulcer dyspepsia, esophageal reflux disease and peptic ulcer disease. *Helicobacter pylori* is an example of a GGT positive bacteria which is associated with disorders of the gastrointestinal tract as described previously. Additionally, *Helicobacter pylori* can be associated with mucosa associated lymphoid tissue (MALT) acne rosacea, Gulf Veteran's Syndrome, Chronic Fatigue Syndrome and halitosis. In one embodiment, GGT positive bacteria normally found as flora in the gastrointestinal tract, which do not cause disorders of the gastrointestinal tract under normal circumstances are not encompassed by this terminology.

The term "mammal," as used herein, refers to an animal, more preferably a warm-blooded animal, most preferably cattle, sheep, pigs, horses, dogs, cats, rats, mice, and humans. Mammals susceptible to infection by GGT positive bacteria, e.g., *Helicobacter pylori,* or susceptible to disorders of the gastrointestinal tract are included as part of this invention.

The term "therapeutically effective amount" is that amount necessary or sufficient to control GGT-positive bacteria in the above methods, e.g., prevent or reduce the GGT positive bacteria's ability to grow. The term "therapeutically effective amount" also can be that amount necessary to eradicate, e.g., kill, the GGT-positive bacteria. An effective amount of the therapeutic agent necessary to control GGT-positive bacteria can vary according to factors such as the type of GGT-positive bacteria, the amount of GGT-positive bacteria already present in the animal, the age, sex, and weight of the animal, and the ability of the compounds of the present invention to control GGT-positive bacteria in the mammal. Dependent upon the desired outcome, the amount of control can be tailored for structure/relationship correlations of the therapeutic agents.

A therapeutically effective amount preferably controls the amount of GGT-positive bacteria and/or a disease state characterized by the presence of GGT-positive bacteria in the infected mammal by at least about 20%, more preferably by at least about 40%, even more preferably by at least about 60%, and still more preferably by at least about 80% relative to untreated subjects. These percentages refer to a decrease in the amount of GGT-positive bacteria found in the infected animal and/or the decrease in symptoms associated with a disease state characterized by the presence of GGT-positive bacteria in the infected animal relative to untreated subjects. For example, a sample of gastric juices can be obtained from an animal infected with GGT-positive bacteria and treated with one of the compounds described supra. A second sample of gastric juices can be obtained from an animal also infected with GGT-positive bacteria which is left untreated with any compound. One skilled in the art would be able to develop the samples on a petri dish (as described in the Examples infra) to determine whether the compound tested controlled the GGT-positive bacteria relative to the untreated sample, e.g., reduction or elimination of colonies relative to the untreated sample. Furthermore, the ability of a compound of the invention to control GGT-positive bacteria associated with disorders of the gastrointestinal tract of a mammal can be evaluated in an animal model system or by standard in vitro assays that may be predictive of efficacy in treating GGT-positive bacteria associated with infection of the gastrointestinal tract in human diseases. Such in vivo model systems include those described by E. Dick-Hegedus & A. Lee, *Scand. J. Gastroenterol.* 26, 909 (1991).

In another embodiment, the invention pertains to a pharmaceutical preparation for the treatment of a state characterized by the presence of GGT-positive bacteria, e.g., *H. pylori*, in a mammal. The pharmaceutical preparation comprises a therapeutically effective amount of a GGT modulating compound and a pharmaceutically acceptable carrier. Preferably, the GGT-positive bacteria is an agent associated with disorders of the gastrointestinal tract. Examples of preferred disorders of the gastrointestinal tract include inflammation of the gastrointestinal tract, ulceration of a portion of the gastrointestinal tract, non-ulcer dyspepsia, esophageal reflux disease, and peptic ulcer disease.

When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount which controls GGT positive bacteria and/or treats a disease state characterized by the presence of a GGT positive bacteria, such as *Helicobacter pylori*.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances includes relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.) A preferred ester group is an acetomethoxy ester group.

In another embodiment, the invention features a method of controlling GGT-positive bacteria. The method involves contacting the bacteria, e.g., *H. pylori*, with a GGT modulating compound. The GGT modulating compound may be, for example, a reversible or irreversible inhibitor of GGT.

The term "reversible inhibitor" includes compounds which bind reversibly to GGT and modulate the activity of GGT.

The term "irreversible inhibitor" includes compounds which bind irreversibly to GGT and modulate the activity of GGT.

The invention also features a method for controlling *Helicobacter pylori* in a mammal, by administering to the mammal a therapeutically effective amount of a GGT-modulating compound.

It also includes a method for treating an ulcer, e.g., an ulcer associated with *H. pylori*, in the gastrointestinal tract of a mammal, by administering to a mammal a therapeutically effective amount of a GGT-modulating compound.

The term "ulcer" includes breaks in the skin or mucous membrane with loss of surface tissue, e.g. degradation of the lining of the esophagus, stomach lining, and/or lining of the small and/or large intestine. Ulcers, such as peptic ulcers, can be caused by GGT positive bacteria such as *Helicobacter pylori*.

The language "an ulcer associated with *Helicobacter pylori*" includes ulcers, inflammation, and/or erosion of the gastrointestinal lining which causes discomfort to the mammal and is associated directly or indirectly with the presence of *Helicobacter pylori* in the mammal.

The language "treating an ulcer associated with *Helicobacter pylori*" includes the alleviation of or diminishment of at least one symptom typically associated with an ulcer associated with *Helicobacter pylori*. The treatment also includes alleviation or diminishment of more than one symptom. Preferably, the treatment cures, e.g., substantially eliminates, the symptoms associated with the ulcer.

The invention also pertains to a packaged pharmaceutical composition for controlling GGT-positive bacteria in a mammal. The packaged pharmaceutical compositions includes a container holding a therapeutically effective amount of a pharmaceutical composition for treating GGT-positive bacteria in a mammal, a pharmaceutical composition comprising at least one GGT modulating compound; and instructions for using said pharmaceutical composition for control of said GGT-positive bacteria, such that GGT-positive bacteria in the mammal is controlled.

The invention is further illustrated by the following examples which in no way should be construed as being further limiting. The contents of all references, pending patent applications and published patent applications, cited throughout this application are hereby incorporated by reference. It should be understood that the in vitro assays and/or correlated animal models used throughout the examples are accepted models and that the demonstration of efficacy in these models is predictive of efficacy in humans.

EXAMPLE

Cell Based GGT Inhibitor Assay

The protocol of the Cell Based GGT Inhibitor Assay (CBGI assay) is adapted from the Methods in Enzymology protocol 252: 66 (1995).

*H. pylori* Sample Preparation

*H. pylori* ATCC 43504 were grown on blood agar plates. For accurate results, the *H. pylori* cells were in a logarithmic, spiral phase. This was achieved by plating cells from a culture that was >75% spiral in a phosphate buffered saline (PBS) solution on blood agar plates and incubating them overnight in microaerophilic conditions at 37° C. The next day, the cells were harvested by adding 1 ml of PBS to the plate and scraping off cells gently with a loop. The cells were then placed in a sterile 50 ml conical tube and the plate was washed ~5 times with 1 ml of PBS. The washes were then pooled in the same 50 ml tube. An $OD_{600}$ was subsequently taken using PBS as the blank. The cells were then resuspended to reach a final $OD_{600}$ of 0.05. A single blood agar plate typically yields approximately 50–75 mls of cells at $A_{600}$ OD=0.05. 3 mls of cells at OD=0.05 are required for each 96-well plate; 30 µl added to each well yields a final OD of 0.015. 4–5 blood agar plates would yield more than enough *H. pylori* cells for 50 96-well microtitre plates.

GGT Assay Method

On each test plate, two known inhibitors were added to separate control wells (4 µl 0.25 mM azaserine and 4 µl 1.25 mM γ-glu-hydroxamate). Control wells containing only cells were also included on each test plate. In each well, 70 µl of buffer was added using an automated dispenser. Then, 30 µl *H. pylori* cells were added at OD $A_{600}$=0.05. After the cells were added to each well, the plate was kept at room temperature for ~30 minutes. The reaction was terminated by dispensing 75 µl 100 mM glycine to each well.

GGT inhibition was determined by analyzing the release of amido-4-methylcoumarin (AMC) at $A_{460}$ nm after excitation at $A_{360}$ in Cytoflour//Walloc fluorescent plate reader. The data was compared to the average of the two control wells from each plate and the γ-glu-hydroxamate control, which should always be ~50%. Any compound that inhibited ≦50% activity was retested.

Solutions

PBS 0.2 g KCl 0.2 g $KH_2PO_4$ 8.0 g NaCl 2.16 g $Na_2HPO_4$–$7H_2O$ or 1.15 g $Na_2HPO_4$ in ~800 ml $H_2O$ pH to 7.2 bring up to 1 liter $H_2O$ sterilize by autoclaving 30 min.

Results

TABLE 1

Binding Data of GGT Modulating Compounds

| Compound | Structure | IC$_{50}$ (μg/ml) |
|---|---|---|
| A | 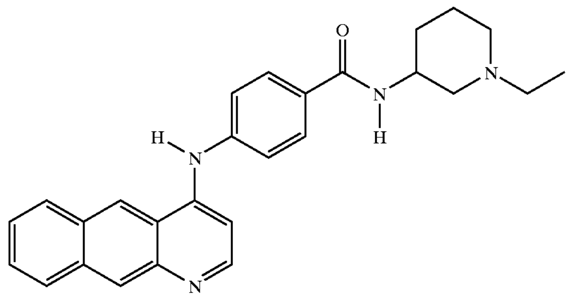 | 0.48 |
| B | 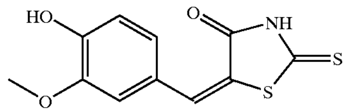 | 6 |
| C | 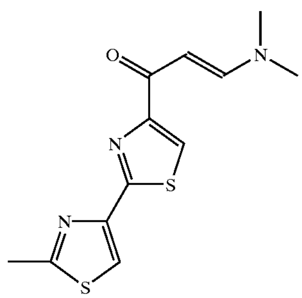 | 5–10 |
| D | 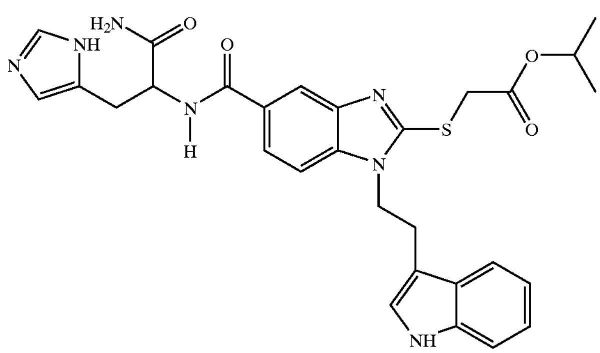 | 2.6 |
| E | 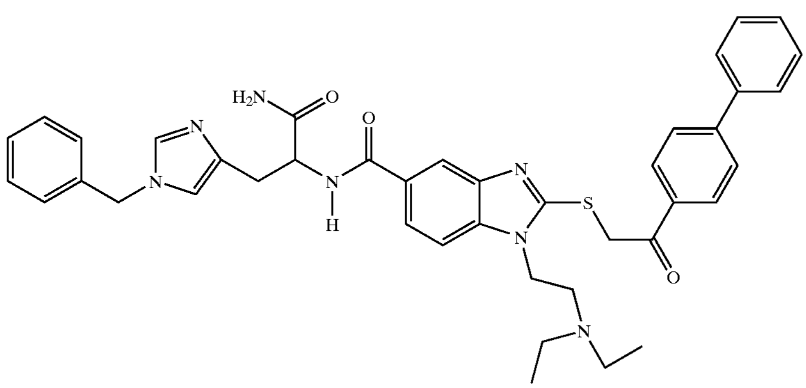 | 8 |

TABLE 1-continued

Binding Data of GGT Modulating Compounds

| Compound | Structure | IC$_{50}$ ($\mu$g/ml) |
|---|---|---|
| F | 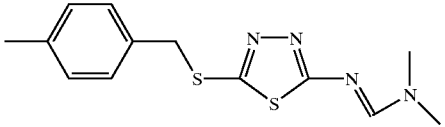 | 0.59 |
| G | 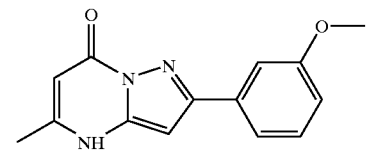 | 0.55 |

What is claimed is:

1. A method for controlling GGT-positive bacteria in a mammal, comprising administering to a mammal a therapeutically effective amount of a GGT modulating compound, such that GGT-positive bacteria in the mammal is controlled.

2. The method of claim 1, wherein said mammal is a human.

3. The method of claim 1, wherein said GGT-positive bacteria is an agent associated with disorders of the gastrointestinal tract.

4. The method of claim 3, wherein said GGT-positive bacteria is *Helicobacter pylori*.

5. The method of claim 1, wherein said GGT modulating compound is of the formula:

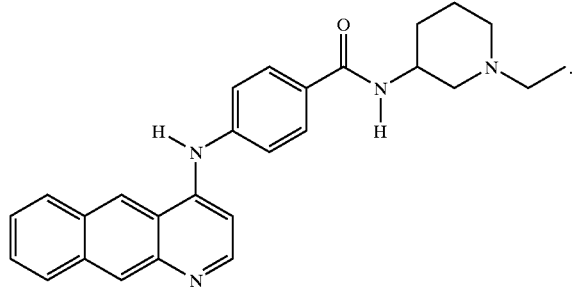

6. The method of claim 1, wherein said GGT modulating compound is of the formula:

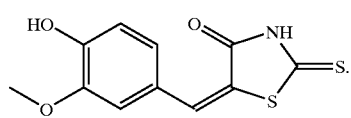

7. The method of claim 1, wherein said GGT modulating compound is of the formula:

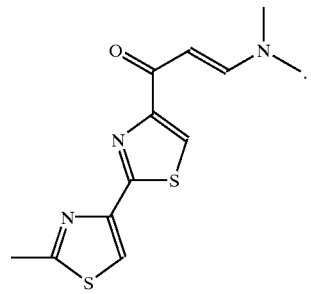

8. The method of claim 1, wherein said GGT modulating compound is of the formula:

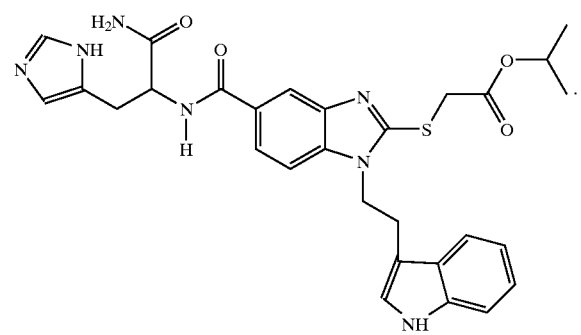

9. The method of claim 1, wherein said GGT modulating compound is of the formula:

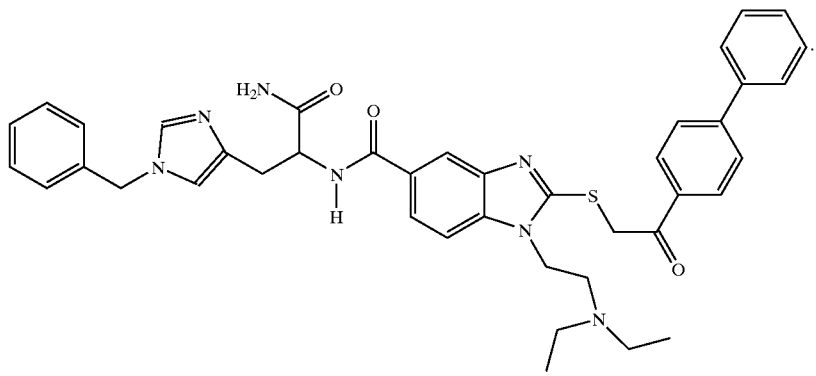

10. The method of claim 1, wherein said GGT modulating compound is of the formula:

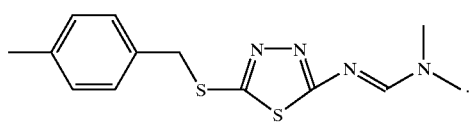

11. The method of claim 1, wherein said GGT modulating compound is of the formula:

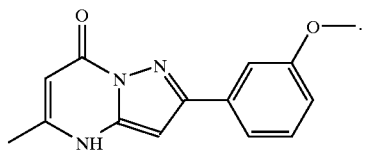

12. A method of controlling GGT-positive bacteria by contacting said bacteria with a GGT modulating compound.

13. The method of claim 12, wherein said GGT-positive bacteria is *H. pylori*.

14. The method of claim 12, wherein said GGT modulating compound is a reversible inhibitor of GGT.

15. The method of claim 12, wherein said GGT modulating compound is an irreversible inhibitor of GGT.

16. The method of claim 12, wherein said GGT modulating compound is of the formula:

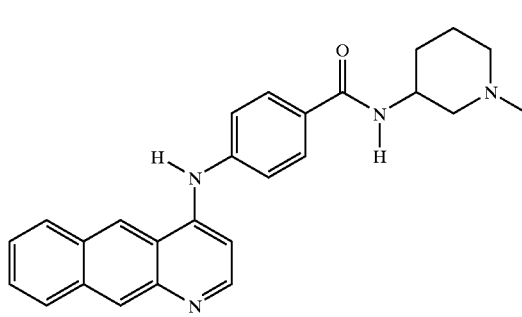

17. The method of claim 12, wherein said GGT modulating compound is of the formula:

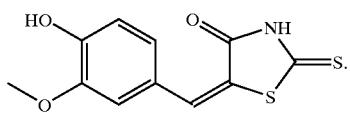

18. The method of claim 12, wherein said GGT modulating compound is of the formula:

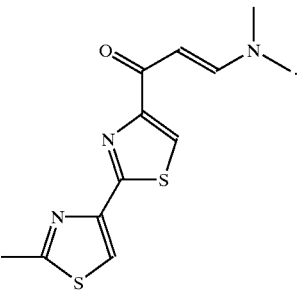

19. The method of claim 12, wherein said GGT modulating compound is of the formula:

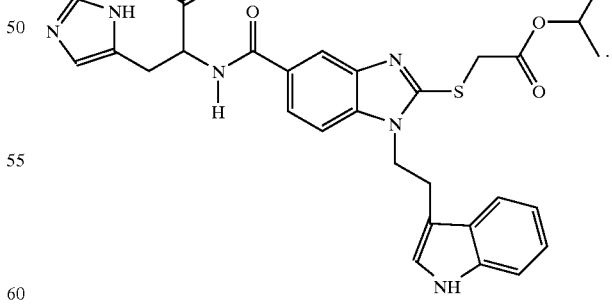

20. The method of claim 12, wherein said GGT modulating compound is of the formula:

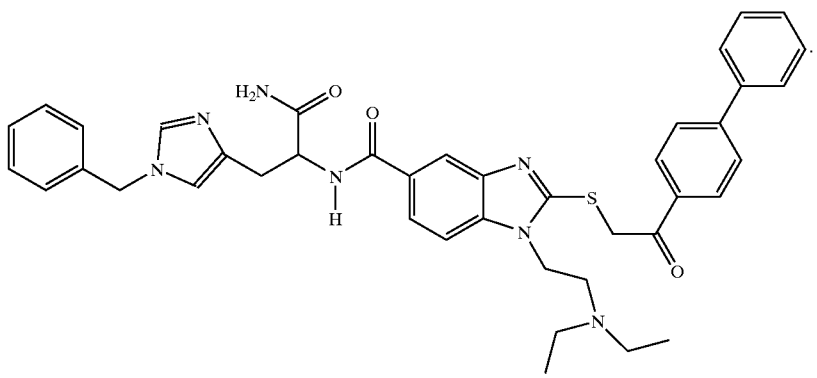

21. The method of claim 12, wherein said GGT modulating compound is of the formula:

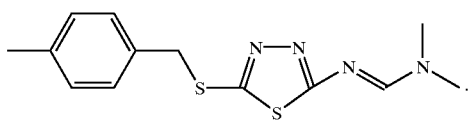

22. The method of claim 12, wherein said GGT modulating compound is of the formula:

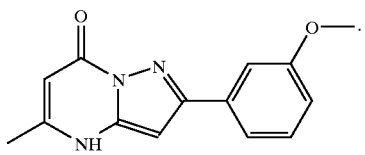

23. A pharmaceutical preparation for the treatment of a state characterized by the presence of GGT-positive bacteria in a mammal, comprising a therapeutically effective amount of a GGT modulating compound and a pharmaceutically acceptable carrier.

24. The pharmaceutical preparation of claim 23, wherein said GGT-positive bacteria is an agent associated with disorders of the gastrointestinal tract.

25. The pharmaceutical preparation of claim 24, wherein said gastrointestinal disorder is selected from the group consisting of inflammation of the gastrointestinal tract, ulceration of a portion of the gastrointestinal tract, non-ulcer dyspepsia, esophageal reflux disease, and peptic ulcer disease.

26. The pharmaceutical preparation of claim 23, wherein said GGT-positive bacteria is *H. pylori*.

27. A method for controlling *Helicobacter pylori* in a mammal, comprising administering to a mammal a therapeutically effective amount of a GGT-modulating compound, such that *Helicobacter pylori* in the mammal is controlled.

28. A method for treating an ulcer associated with *Helicobacter pylori* in a mammal, comprising administering to a mammal a therapeutically effective amount of a GGT-modulating compound, such that an ulcer associated with *Helicobacter pylori* in the mammal is treated.

29. A packaged pharmaceutical composition for controlling GGT-positive bacteria in a mammal, comprising:

a container holding a therapeutically effective amount of a pharmaceutical composition for treating GGT-positive bacteria in a mammal, said pharmaceutical composition comprising at least one GGT modulating compound; and instructions for using said pharmaceutical composition for control of said GGT-positive bacteria, such that GGT-positive bacteria in the mammal is controlled.

* * * * *